United States Patent [19]

Miyamoto et al.

[11] Patent Number: 5,308,848
[45] Date of Patent: * May 3, 1994

[54] PYRIMIDINEDIONE DERIVATIVES AND ANTIARRYTHMIC AGENTS CONTAINING THE SAME

[75] Inventors: Michihiko Miyamoto; Tsutomu Katakami; Nobuya Kawauchi; Tadahito Nobori; Joji Kamiya; Masaaki Ishii, all of Mobara, Japan

[73] Assignee: Mitsui Toatsu Chemicals, Incorporated, Tokyo, Japan

[*] Notice: The portion of the term of this patent subsequent to Apr. 16, 2008 has been disclaimed.

[21] Appl. No.: 927,738

[22] Filed: Aug. 12, 1992

Related U.S. Application Data

[63] Continuation of Ser. No. 679,679, Apr. 4, 1991, abandoned, and a continuation-in-part of Ser. No. 425,730, Oct. 24, 1989, Pat. No. 5,008,267.

[30] Foreign Application Priority Data

Apr. 13, 1990 [JP] Japan ................ 2-96497

[51] Int. Cl.$^5$ ............ A61K 31/505; C07D 239/10
[52] U.S. Cl. .................... 514/269; 514/274; 544/311; 544/312; 544/314
[58] Field of Search ........... 540/575; 544/311, 312, 544/314; 514/218, 269, 274

[56] References Cited

U.S. PATENT DOCUMENTS 4,216,314  8/1980  Raabe et al. ................ 544/312
5,008,267  4/1991  Katakami et al. ............ 544/295

OTHER PUBLICATIONS

Kataue et al., Chemical Abs., 113(5), 40725, 1989.
Mitsui Toatsu, Chemical Abs., 103(1), 6363n, 1984.
Cassela, Chemical Abs., 90(15), 121639, 1978.
Raabe et al., Chemical Abs., 90(15), 121636, 1978.
The Pharmacological Basis of Therapeutics; Goodman and Gillman, p. 840, 1990.
Cardiova. Pharmacology, Second Edition, Lucchesi et al., p. 329, 1984.
Drugs, 35:286-319, 1988, p. 286.
Goldberger et al., International Journal of Cardiology, vol. 13, pp. 47-55, 1986.
Lynch et al., Journal of Cardiovascular Pharmacology, vol. 6, pp. 1132-1141, 1984.
Mitsunobu, Synthesis, pp. 1-28, 1981.
Platou et al., Journal of Cardiovascular Pharmacology, vol. 8, pp. 459-465, 1986.

Primary Examiner—Mukund J. Shah
Assistant Examiner—Y. N. Gupta
Attorney, Agent, or Firm—Nixon & Vanderhye

[57] ABSTRACT

A pyrimidinedione derivative compound has a basic backbone in which a phenyl group part and a pyrimidinedione part are linked by a linking structure comprising an alkyl chain containing two nitrogen atoms. This linking structure is represented by

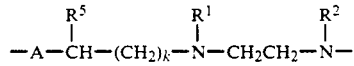

[wherein A is —(CH$_2$)$_n$—, —CO— or —O—(CH$_2$)$_m$—; each of R$^1$ and R$^2$ is independently a hydrogen atom or a lower alkyl group which may be substituted by a hydroxyl group, or R$^1$ and R$^2$ may be so linked with each other as to make an alkylene chain and thus form a heterocyclic structure; R$^5$ is a halogen atom, a hydroxyl group, a lower alkyloxycarbonyl group, a lower alkyloxy group which may be substituted by a lower alkyloxy group, or a lower alkyl group which may be substituted by a hydroxyl group, or R$^5$ may be so linked with R$^1$ as to make an alkylene chain and thus form a heterocyclic structure; n is 0, 1, 2 or 3 (when R$^5$ is the hydroxyl group, n≠0); m is 0, 1, 2 or 3; and k is 0, 1, 2 or 3 (however, a compound in which A is —O—(CH$_2$)$_m$— and R$^5$ is the hydroxyl group is excluded from the pyrimidinedione derivative)]. The pyrimidinedione derivative and its acid addition salt are useful for a medical treatment of cardiac arrhythmias.

4 Claims, No Drawings

PYRIMIDINEDIONE DERIVATIVES AND ANTIARRYTHMIC AGENTS CONTAINING THE SAME

This application is a continuation of earlier application Ser. No. 07/679,679, filed Apr. 4, 1991, abandoned, and is a continuation-in-part of application Ser. No. 07/425,730 filed Oct. 24, 1989, now U.S. Pat. No. 5,008,267.

BACKGROUND OF THE INVENTION (i) Field of the Invention

The present invention relates to novel pyrimidinedione derivatives and acid addition salts thereof, to methods of preparing the same, and to pharmaceutical agents containing the same which are effective for the treatment of arrhythmia.

(ii) Description of the Related Art

The mechanism of the occurrence of arrhythmia is complicated. Abnormalities in stimulation production and disorders in the conducting system or combinations thereof are considered to be responsible.

As to disorders in excitation conduction, the reentry theory is representative.

One of the conditions of occurrence of arrhythmia is irregularity in the refractory period in various parts of the heart. In addition, one-directional block, shortened refractory period, delay in conduction and the presence of circus movement are complicatedly involved.

Heretofore, various antiarrythmic agents have been used for the treatment of arrhythmia.

The antiarrythmic agents are classified into four groups according to their modes of action.

That is, E. M. Vaughan Williams (Vaughan Williams E. M.; "Advances in drug research, Vol. 9", ed. by Harper N. J., Simmonds A. B., Academic Press, London, 1974, pages 69–101) have classified the antiarrythmic agents into the following four groups in accordance with their actions against the action potential of cardiac muscle or against the ionic current which generates the action potential.

Class I: Sodium channel depressors

These agents are efficacious in repressing a sodium current. However, they have no or only minute effects on the retention time of the normal action potential and decrease the maximum rising velocity ($V_{max}$) of the sodium current. The antiarrythmic agents which belong to this class have a high antiarrythmic activity but at the same time strongly repress cardiac functions. Careful consideration is required in administering to patients with cardiac failure or hypotension.

Class II: Beta-blocking agents

The agents in this class, represented by propranolol, are efficacious in the beta-blocking action and are useful in treating patients with arrhythmia in which the sympathetic nerve is involved. However, the care must be taken for use since these agents have side-effects caused by the beta-blocking action, such as depression of cardiac functions, induction of bronchial asthmatic attack and hypoglycemic seizures.

Class III: Pharmaceutical agents for prolonging the retention time of the action current.

These agents are efficacious in remarkably prolonging the retention time of the action current of the cardiac muscle and in prolonging an effective refractory period. Re-entry arrhythmia is considered to be suppressed by the action of the pharmaceutical agents of Class III. The medicaments of this Class III include aminodarone and bretylium. However, all the agents have severe side effects, and therefore, careful consideration is required for use.

Class IV: Calcium antagonists

These agents control a calcium channel and suppress arrhythmia due to automatic sthenia of sinoatrial nodes and to ventricular tachycardia in which atrial nodes are contained in the re-entry cycle.

Among these antiarrythmic agents, pharmaceutical agents of the Class III type are considered to be particularly important and most efficacious, and known to be effective on ventricular arrhythmia which is most fatal.

SUMMARY OF THE INVENTION

Various medicinal agents have already been developed and utilized as antiarrythmic agents.

Search for ideal antiarrythmic agents has been pursued for treatment of arrythmia which has complicated generating mechanisms and requires administration of such agents for a long period of time. However, satisfactory results have not been achieved so far.

The present invention has been accomplished in view of the present situation regarding antiarrythmic agents. Thus, an object of the present invention is to provide a novel compound which is useful as a Class III type antiarrythmic agent and to provide a process for producing the same.

In the course of the intensive study to solve the above-mentioned problems, the present inventors have found compounds of the formula (1) shown below and acid addition salts thereof Furthermore, they have investigated the pharmacological properties of these compounds, and as a result, they have found that these compounds have pharmacological characteristics for markedly prolonging the retention time of the action potential of cardiomuscular cells and for markedly prolonging the ventricular refractory period in animal experiments using adult dogs. In consequence, the present invention has been achieved on the basis of the above-mentioned knowledge.

The compounds of the present invention can be utilized to provide antiarrythmic agents and therapeutic agents for cardiac insufficiency.

DETAILED DESCRIPTION OF THE PREFERRED EMBODIMENTS

The compounds of the present invention are compounds represented by the following formula (1) and acid addition salts thereof:

$$X-\text{C}_6\text{H}_4-A-\underset{R^5}{\text{CH}}-(\text{CH}_2)_k-\underset{R^1}{N}-\text{CH}_2\text{CH}_2-\underset{R^2}{N}-\text{[pyrimidinedione ring with } R^3, R^4\text{]} \quad (1)$$

[wherein A is $-(\text{CH}_2)_n-$, $$-\underset{\overset{\|}{O}}{C}-$$

or $-O-(\text{CH}_2)_m-$; each of $R^1$ and $R^2$ is independently a hydrogen atom or a lower alkyl group which may be substituted by a hydroxyl group, or $R^1$ and $R^2$ may be so linked with each other as to make an alkylene chain and thus form a heterocyclic structure; each of $R^3$ and $R^4$ is independently a hydrogen atom or a lower alkyl group; $R^5$ is a halogen atom, a hydroxyl group, a lower alkyloxycarbonyl group, a lower alkyloxy group which may be substituted by a lower alkyloxy group, or a lower alkyl group which may be substituted by a hydroxyl group, or $R^5$ may be so linked with $R^1$ as to make an alkylene chain and thus form a heterocyclic structure; X is a hydrogen atom, a halogen atom or a nitro group; n is 0, 1, 2 or 3 (when $R^5$ is the hydroxyl group, n≠0); m is 0, 1, 2 or 3; and k is 0, 1, 2 or 3 (however, compounds in which A is $-O-(CH_2)_m-$ and $R^5$ is the hydroxyl group are excluded from the compounds of the present invention)].

In the compounds of the formula (1), examples of the lower alkyl group include straight-chain and branched alkyl groups having 1 to 5 carbon atoms such as methyl, ethyl, propyl, butyl, isopropyl, isobutyl, tertiary butyl and secondary butyl groups.

Furthermore, examples of the lower alkyl group substituted by the hydroxyl group include 2-hydroxyethyl, 3-hydroxypropyl, 2-hydroxypropyl and 4-hydroxybutyl groups.

Examples of the halogen atom include fluorine, chlorine and bromine atoms.

Examples of the lower alkyloxy group include oxygen atoms substituted by the above-mentioned lower alkyl groups.

Examples of the lower alkyloxycarbonyl group include carbonyl groups substituted by the above-mentioned lower alkyloxy groups.

Examples of the alkylene chain for linking $R^1$ with $R^2$ or linking $R^1$ with $R^5$ include ethylene and propylene chains.

The expression "pharmaceutically acceptable" used to describe the pharmaceutically acceptable acid addition salts in the compounds of the above-mentioned formula (1) means that remarkable side effects or toxicity does not appear and that its pharmaceutical activities are not extinguished, when administered to men. These acid addition salts can be produced by neutralization of the corresponding free bases.

Typical examples of the compounds of the present invention will be mentioned, but no restriction is put on these compounds.

1,3-dimethyl-6-[4-(2-hydroxy-3-phenylpropyl)piperazin-1-yl]-2,4(1H,3H)-pyrimidinedione, 1,3-dimethyl-6-[2-(3-hydroxy-4-phenylbutylamino)ethylamino]-2,4(1H,3H)-pyrimidinedione, 1,3-dimethyl-6-[N-ethyl-2-(2-hydroxy-4-phenylbutylamino)ethylamino]-2,4(1H,3H)-pyrimidinedione, 1,3-dimethyl-6-[2-(N-methyl-2-hydroxy-4-phenylbutylamino)ethylamino]-2,4(1H,3H)-pyrimidinedione, 1,3-dimethyl-6-[4-(2-hydroxy-4-phenylbutyl)piperazin-1-yl]-2,4(1H,3H)-pyrimidinedione, 1,3-dimethyl-6-[2-(2-hydroxy-4-phenylbutylamino)ethylamino]-2,4(1H,3H)-pyrimidinedione, 1,3-dimethyl-6-[4-(2-fluoro-4-phenylbutyl)piperazin-1-yl]-2,4(1H,3H)-pyrimidinedione, 1,3-dimethyl-6-[4-(2-ethoxycarbonyl-2-phenylethyl)piperazin-1-yl]-2,4(1H,3H)-pyrimidinedione, 1,3-dimethyl-6-[4-(3-hydroxy-4-phenylpropyl)piperazin-1-yl]-2,4(1H,3H)-pyrimidinedione, 1,3-dimethyl-6-[4-(1-ethoxycarbonyl-2-phenylethyl)piperazin-1-yl]-2,4(1H,3H)-pyrimidinedione, 1,3-dimethyl-6-[4-(1-benzyl-2-hydroxyethyl)piperazin-1-yl]-2,4(1H,3H)-pyrimidinedione, 1,3-dimethyl-6-[4-(1-ethoxycarbonyl-2-phenylethyl)piperazin-1-yl]-2,4(1H,3H)-pyrimidinedione, 6-[4-(1-hydroxy-5-phenylpentane-3-yl)homopiperazin-1-yl]-2,4(1H,3H)-pyrimidinedione, 3-propyl-6-[2-(N-[3-hydroxypropyl]-1-hydroxy-4-phenylbutan-2-ylamino)ethylamino]-2,4(1H,3H)-pyrimidinedione, 1,3-diisopropyl-6-[N-isopropyl-2-(1-hydroxy-4-phenylbutan-2-ylamino)ethylamino]-2,4(1H,3H)-pyrimidinedione, 1,3-dimethyl-6-[2-(N-[2-hydroxyethyl]-1-hydroxy-4-[nitrophenyl]butan-2-ylamino)ethylamino]-2,4(1H,3H)-pyrimidinedione, 1,3-dimethyl-6-[4-(1-hydroxy-4-phenylbutan-2-yl)piperazin-1-yl]-2,4(1H,3H)-pyrimidinedione, 1,3-dimethyl-6-[4-(3-[4-chlorophenoxy]-2-(2-methoxyethoxy)propyl)piperazin-1-yl]-2,4(1H,3H)-pyrimidinedione, 1,3-dimethyl-6-[4-(3-[4-nitrophenoxy]-2-(propyloxy)propyl)piperazin-1-yl]-2,4(1H,3H-pyrimidinedione, 1,3-dimethyl-6-[2-(4-[4-fluorobenzoyl]-piperide-1-yl)ethylamino]-2,4-(1H,3H)-pyrimidinedione, 1,3-dimethyl-6-[2-(N-[2-hydroxyethyl]-3-(4-nitrophenyl)butylamino)ethylamino]-2,4(1H,3H)-pyrimidinedione, 1,3-dimethyl-6-[2-(N-[2-hydroxyethyl]-3-(4-nitrophenyl)pentylamino)ethylamino]-2,4(1H,3H)-pyrimidinedione, and 1,3-dimethyl-6-[2-(N-[2-hydroxyethyl]-4-(4-nitrophenyl)butan-2-ylamino)ethylamino]-2,4(1H,3H)-pyrimidinedione.

Examples of the acids from which these pharmaceutically acceptable salts can be prepared include organic acids and inorganic acids, such as hydrochloric acid, hydrobromic acid, phosphoric acid, sulfuric acid, nitric acid, methanesulfonic acid, maleic acid, oxalic acid, malonic acid, succinic acid, fumaric acid, tartaric acid, citric acid, lactic acid and benzenesulfonic acid.

As shown in the above-mentioned formula (1), the compound of the present invention has a fundamental skeleton in which a phenyl moiety is linked with a pyrimidinedione moiety via the structure mainly comprising an alkyl chain containing at least two nitrogen atoms, and it can be presumed that the above-mentioned fundamental skeleton exerts pharmacological effects.

That is, when the compounds shown by the above-mentioned formula (1) were applied to the following arrhythmia pathological models, all the compounds demonstrated efficacy.

Atrial Fibrillation Model

Atrial fibrillation model animals were made in accordance with the method of A. L. Goldberger et al. (International Journal of Cardiology, Vol. 13, p. 47-55, 1986) by anesthetizing adult mongrel dogs with pentobarbital sodium (30 mg/kg, intravenous administration). Using these atrial fibrillation model animals, the effects of the compounds of the present invention on the atrial fibrillation model were investigated by administering the compounds intravenously at a dose of 0.1-10 mg/kg. As a result, it was confirmed that all the compounds of the present invention had therapeutic effects on atrial fibrillation. Ventricular Tachycardia Model Adult mongrel dogs were anesthetized with pentobarbital sodium (30 mg/kg, intravenous administration). A left thoracotomy was performed in the fourth intercostal space under artificial respiration, and the left anterior descending coronary artery was ligated at the border of the atrial appendage. The blood was then recirculated 120 minutes after the ligation, so that a cardiac infarction lesion was formed to readily induce tachycardia in each animal.

Thereafter, the ventricular tachycardia model animals were made by inducing ventricular tachycardia in accordance with the method of Lynch (Journal of Cardiovascular Pharmacology, Vol. 6, p. 1132-1141, 1984).

Using these model animals, it was confirmed that the compounds of the present invention had therapeutic effects on ventricular tachycardia when administered intravenously at a dose of 0.1 to 3 mg/kg.

As understood from the foregoing, the compounds of the present invention have effective therapeutic effects on the arrhythmia pathology model, i.e., atrial fibrillation model and ventricular tachycardia model, thus they are useful for the treatment and prevention of arrhythmia.

Furthermore, the effects of the compounds of the present invention on cardiac functions were investigated, so that the following results were obtained.

Mongrel dogs (body weights: 8–15 kg) were anesthetized with pentobarbital sodium (30 mg/kg, intravenous administration). A microsensor catheter was then inserted through the common carotid artery into the left ventricle of each animal so that primary differential values (dp/dt) of the inner pressure of the left ventricle and electrocardiograms were recorded. The compounds of the present invention were administered intravenously to the dogs (1 mg/kg) and changes in the dp/dt and electrocardiograms were investigated.

As a result, it was revealed that the compounds of the present invention significantly increased the values of dp/dt max and significantly extended QTc on the electrocardiograms.

Consequently, it was confirmed that the compounds of the present invention had an antiarrythmic action and particularly were useful as Class III type antiarrythmic agents. Furthermore, the significant increase in dp/dt max demonstrated that the compounds of the present invention had a positive inotropic action and accordingly they were useful as therapeutic agents for cardiac insufficiency.

As mentioned above, in general, most of patients with arrhythmia have deficiency in cardiac functions. In the case where, for example, antiarrythmic agents classified in Class I or II are given to such patients, the greatest care has to be taken for use because these agents exert more or less antiarrythmic action as well as a negative inotropic action (action to further repress cardiac functions) (Eivind S. Platous, Journal of Cardiovascular Pharmacology, Vol. 8, No. 3, p. 459, 1986).

On the contrary, as mentioned above, the compounds of the present invention have a positive inotropic action to significantly increase the dp/dt max as well as an antiarrythmic action. Accordingly, it can be expected that these compounds provide satisfactory results to the arrhythmia patients whose cardiac functions are depressed.

Representative examples of processes for the production of the compounds of the formula (1) of the present invention will be described hereinafter, but the present invention should not be limited to these examples.

Of the compounds having the above-mentioned formula (1), a compound represented by the formula (11)

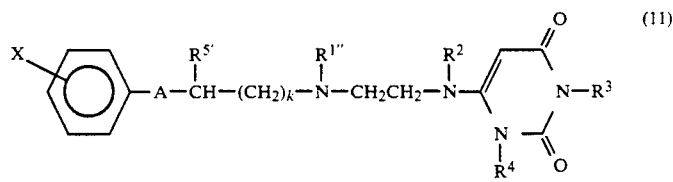

[wherein X, A, $R^2$, $R^3$, $R^4$ and k are defined as in the above-mentioned formula (1), $R^{1''}$ is a hydrogen atom or a lower alkyl group which may be substituted by a hydroxyl group, or $R^{1''}$ and $R^2$ may be so linked with each other as to make an alkylene chain and thus form a heterocyclic structure, $R^{5'}$ is a halogen atom, a hydroxyl group, a lower alkyloxycarbonyl group, a lower alkyloxy group which may be substituted by a lower alkyloxy group, or a lower alkyl group which may be substituted by a hydroxyl group, and $R^{5'}$ is not linked with $R^{1''}$]

can be prepared in accordance with a process containing the following step (a).

Step (a):

A compound represented by the formula (2)

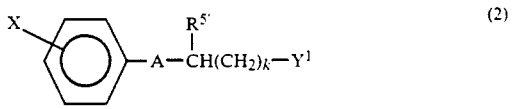

[wherein $Y^1$ is a halogen atom or a substituent which can become a leaving group when reacted with a compound of the following formula (3), and X, A, $R^{5'}$ and k are defined as in the above formula (11)]

and a compound represented by the formula (3)

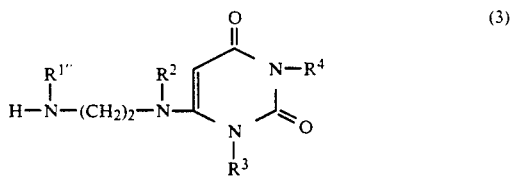

[wherein $R^2$, $R^3$ and $R^4$ are defined as in the above formula (1), and $R^{1''}$ are defined as in the above formula (11)]

are mixed with each other without using any solvent, or alternatively dissolved or suspended in a suitable solvent or dispersant, and reaction is then carried out to obtain the compound of the formula (1).

With regard to $Y^1$ in the above-mentioned formula (2), examples of the substituent which can become the leaving group include an arylsufonyloxy group such as a paratoluenesulfonyloxy group, and an alkylsulfonyloxy group such as a methanesulfonyloxy group.

This reaction is carried out at a temperature of from room temperature to the reflux temperature of the reaction mixture, and for example, the reaction temperature is preferably selected from the range of from 20° to 150° C.

Furthermore, when a base is allowed to coexist in the reaction solution, the reaction can proceed more preferably.

As the suitable solvent or dispersant used in the reaction, any one can be used without restriction, so long as it is inactive to this reaction Examples of the usable solvent and dispersant include alcohols such as methanol and ethanol, tetrahydrofuran, dimethylformamide, chloroform, dichloromethane, dioxane, benzene and dimethyl sulfoxide.

Examples of the base having the effect of accelerating this reaction include triethylamine, pyridine, potassium carbonate, sodium carbonate and sodium hydroxide.

The compound of the above-mentioned formula (1) can be prepared in accordance with a process containing the following step (b).

Step (b):

A compound represented by the formula (4)

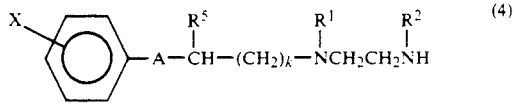

[wherein A, $R^1$, $R^2$, $R^5$, X and k are defined as in the above-mentioned formula (1)]
and a compound represented by the formula (5)

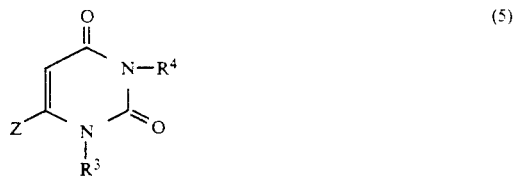

[wherein $R^3$ and $R^4$ are defined as in the above-mentioned formula (1), and Z is a halogen atom]
are mixed with each other without using any solvent, or alternatively dissolved or suspended in a suitable solvent or dispersant, and reaction is then carried out to obtain the compound of the formula (1).

This reaction is carried out at a temperature of from room temperature to the reflux temperature of the reaction mixture, and for example, the reaction temperature is preferably selected from the range of from 20° to 150° C.

Furthermore, when a base is allowed to coexist in the reaction solution, the reaction can proceed more preferably.

As the suitable solvent or dispersant used in the reaction, any one can be used without restriction, so long as it is inactive to this reaction. Examples of the usable solvent and dispersant are recited in the paragraph regarding the above-mentioned step (a).

Examples of the usable base having the effect of accelerating this reaction are recited in the paragraph regarding the above-mentioned step (a).

Of the compounds having the above-mentioned formula (1), a compound represented by the formula (6)

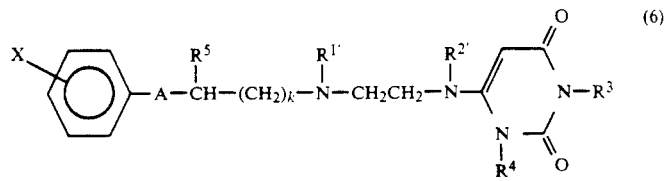

[wherein each of $R^{1'}$ and $R^{2'}$ is independently a hydrogen atom or a lower alkyl group which may be substituted by a hydroxyl group, but $R^{1'}$ is not linked with $R^{2'}$; $R^5$ is a halogen atom, a hydroxyl group, a lower alkyloxycarbonyl group, a lower alkyloxy group which may be substituted by a lower alkyloxy group or a lower alkyl group which may be substituted by a hydroxyl group, or $R^5$ may be linked with $R^{1'}$ to form a heterocyclic structure of an alkylene chain; A, $R^3$, $R^4$ and X are defined in the above-mentioned formula (1)]
can be prepared in accordance with a process containing the following step (c).

Step (c):

A compound represented by the formula (7)

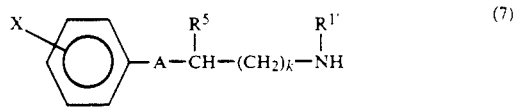

[wherein A, X, $R^{1'}$, $R^5$ and k are defined as in the above formula (6)]
and a compound represented by the formula (8)

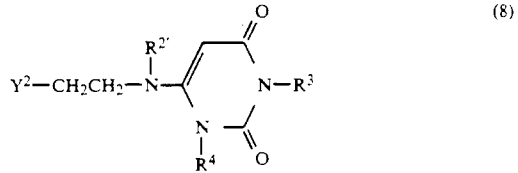

[wherein $Y^2$ is a halogen atom or a substituent which can become a leaving group when reacted with a compound of the above-mentioned formula (7), and $R^{2'}$, $R^3$ and $R^4$ are defined as in the above formula (6)]
are mixed with each other without using any solvent, or alternatively dissolved or suspended in a suitable solvent or dispersant, and reaction is then carried out to obtain the compound of the formula (6).

This reaction is carried out at a temperature of from room temperature to the reflux temperature of the reaction mixture, and for example, the reaction temperature is preferably selected from the range of from 50° to 170° C.

Furthermore, when a base is allowed to coexist in the reaction solution, the reaction can proceed more preferably.

As the suitable solvent or dispersant used in the reaction, any one can be used without restriction, so long as it is inactive to this reaction Examples of the usable solvent and dispersant are recited in the paragraph regarding the above-mentioned step (a).

Examples of the usable base having the effect of accelerating this reaction are recited in the paragraph regarding the above-mentioned step (a). Examples of the usable substituent $Y^2$ which can become the leaving group are recited in the paragraph regarding the above-mentioned $Y^1$.

Of the compounds having the above-mentioned formula (1), a compound represented by the formula (10)

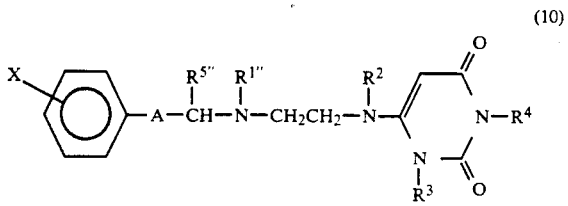

[wherein X, A, $R^2$, $R^3$ and $R^4$ are defined as in the above-mentioned formula (1), $R^{1''}$ is defined as in the above formula (11), $R^{5''}$ is a lower alkyloxycarbonyl group, a lower alkyl group which may be substituted by a hydroxyl group, or a lower alkyloxy group which may be substituted by a lower alkyloxy group, and $R^{5''}$ is not linked with $R^{1''}$]

can be prepared in accordance with a process containing the following step (d). Step (d):

A compound represented by the formula (9)

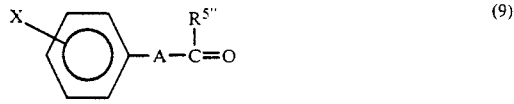

[wherein X, A and $R^{5''}$ are defined as in the above formula (10)]

and a compound represented by the formula (3) are dissolved or suspended in a suitable solvent or dispersant, and reaction is then carried out in the presence of a reducing agent to obtain the compound of the formula (10).

This reaction is carried out at a temperature of from 0° C. to the reflux temperature of the reaction mixture, and for example, the reaction temperature is preferably selected from the range of from 0° to 60° C.

As the reducing agent for use in this reaction, there can be utilized reducing agents which are used in the usual reductive amination, and suitable examples of the reducing agent include sodium borohydride and sodium borocyanohydride.

As the suitable solvent or dispersant used in the reaction, any one can be used without restriction, so long as it is inactive to this reaction. Examples of the usable solvent and dispersant include alcohols such as methanol and ethanol, tetrahydrofuran, dimethylformamide, chloroform, dichloromethane, dioxane, benzene and dimethyl sulfoxide.

In the above-mentioned respective formulae, $R^1$ may link with either $R^2$ or $R^5$ to form a heterocyclic ring, $R^{1'}$ may link with $R^5$ alone to form the heterocyclic ring, $R^{1''}$ may link with $R^2$ alone to form the heterocyclic ring, and $R^{5'}$, $R^{5''}$ and $R^{2'}$ do not link with other groups to form the heterocyclic ring.

On the other hand, a pharmaceutically acceptable acid addition salt of the compound of the above-mentioned formula (1) can be produced by allowing the compound of the formula (1) to react with an inorganic or organic acid such as hydrochloric acid, hydrobromic acid, phosphoric acid, sulfuric acid, acetic acid, citric acid, maleic acid, fumaric acid, oxalic acid or methanesulfonic acid in water, an organic solvent or a mixture thereof.

When the compound of the formula (1) of the present invention or the acid addition salt thereof is used as a therapeutic agent to treat patients with cardiac malfunctions such as arrhythmia and cardiac insufficiency, the dose and form of the agent depend on properties of the compound of the present invention which is used as an active ingredient and depend on symptoms of the patients to be treated. For example, the therapeutic agent can be orally administered in the form of tablets, granules, powders, suspensions or capsules, or parenterally in the form of depositories, injections or fluids for infusion.

Daily dose of the compound(s) of the present invention may range from 1 to 1000 mg, preferably from 10–500 mg, in oral administration for an adult; and from 1 to 1000 mg, preferably from 1–300 mg, in parenteral administration for an adult.

General processes for producing pharmaceutical compositions of the present invention include a method in which the compound of the present invention is dissolved in an appropriate amount of an oil selected from the group consisting of cotton seed oil, corn oil, peanut oil, olive oil and the like so as to prepare non-aqueous injections each containing 0.1–100 mg of the compound of the present invention per one milliliter; a method in which water is added to the compound of the present invention and the resulting solution is then emulsified in an appropriate surfactant to prepare aqueous injections each containing 0.1–100 mg of the compound of the present invention per one milliliter; or a method in which crystallized cellulose and soft anhydrous silicic acid as adsorbents are added to the compound of the present invention, corn starch as an excipien vehicle is further added, and magnesium stearate is finally added, thereby preparing tablets each containing 1–200 mg of the compound of the present invention. However, the pharmaceutical preparations of the present invention can be obtained by any ordinary method in addition to the above-mentioned methods. A mixture of two or more of the compounds of the present invention may be contained in a pharmaceutical composition.

Now, the present invention will be described in more detail in reference to examples, but the scope of the present invention should not be limited to these examples.

EXAMPLE 1

Preparation of
1,3-Dimethyl-6-[4-(2-hydroxy-4-phenylbutyl)piperazin-1-yl]-2,4(1H,3H)-pyrimidinedione.hydrochloride
Compound 1)

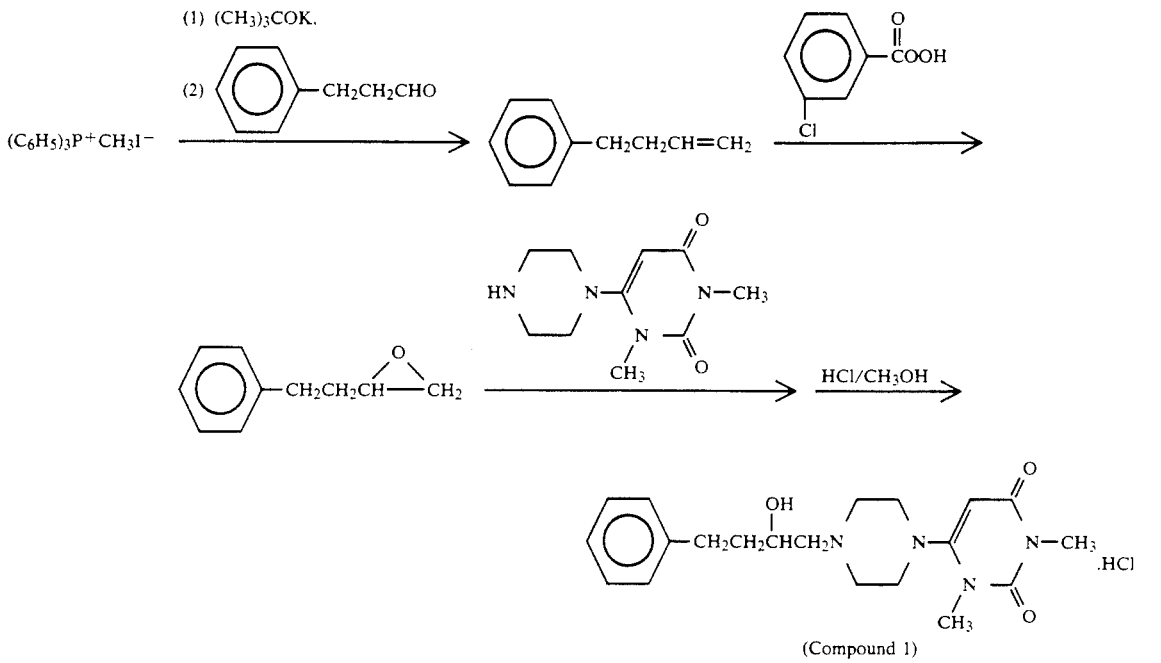

(1) Preparation of 4-phenyl-1-butene 40.4 g of methyltriphenylphosphonium iodide was suspended in 300 ml of anhydrous tetrahydrofuran, and 11.2 g of t-butoxypotassium was added thereto at room temperature. 50 ml of an anhydrous tetrahydrofuran solution containing 10.72 g of 2-phenylpropionaldehyde was added to the resulting suspension at 0° C., followed by stirring at room temperature for 2 hours. Afterward, 20 ml of water was added thereto, and the solution was concentrated to dryness under reduced pressure and 500 ml of ether was added to the resulting residue. The thus obtained ether solution was then washed with water and dried over anhydrous sodium sulfate, and the solvent was distilled off. Next, hexane was added to the residue, and insolubles were removed therefrom by filtration. The filtrate was concentrated to dryness, and the resulting yellow oily product was then purified through a silica gel column chromatograph (hexane) to obtain 9.2 g of a colorless oily product of 4-phenyl-1-butene.

Analytical results of obtained 4-phenyl-1-butene

NMR (CDCl$_3$) δ ppm: 2.20 (m, 2 H), 2.70 (m, 2 H), 5.04 (m, 2 H), 5.90 (m, 1 H), 7.29 (m, 5 H).

IR neat ν max (cm$^{-1}$): 3020, 2920, 1640, 1605, 1500 1450, 995, 910, 700.

(2) Preparation of 1,2-epoxy-4-phenylbutane 2.62 g of 4-phenyl-1-butene obtained in the previous section (1) was dissolved in 30 ml of chloroform, and 4.6 g of m-chloroperbenzoic acid was added thereto at 0° C., followed by stirring at the same temperature for 30 minutes and additionally at room temperature for 3 hours. Afterward, the solvent was distilled off from the reaction solution, and 200 ml of ether was added to the resulting residue. The solution was then washed with a 1 N sodium hydroxide solution and further with water. The thus water-washed ether solution was then concentrated to dryness under reduced pressure to obtain 2.46 g of colorless oily 1,2-epoxy-4-phenylbutane. This compound was fed to a next reaction without further purification.

(3) Preparation of 1,3-dimethyl-6-[4-(2-hydroxy-4-phenylbutyl)piperazin-1-yl]-2,4(1H,3H)-pyrimidine-dione.hydrochloride Compound 1)

1.48 g of 1,2-epoxy-4-phenylbutane obtained in the previous section (2) and 1.8 g of 1,3-dimethyl-6-(1-piperazinyl)-2,4(1H,3H)-pyrimidinedione were dissolved in 40 ml of ethanol, and the solution was then refluxed for 3 hours. Next, the solvent was distilled off from the reaction solution, and the resulting residue was then purified through a silica gel column chromatograph (chloroform/methanol=100/1 to 20/1 in volume ratio) and additionally recrystallized from a mixed solvent of chloroform and hexane, thereby obtaining 2.14 g of colorless crystalline 1,3-dimethyl-6-[4-(2-hydroxy-4-phenylbutyl)piperazine-1-yl]-2,4(1H,3H)-pyrimidinedione.

Analytical results of the obtained pyrimidinedione derivative

Melting point: 133° to 134° C.

NMR (CDCl$_3$) δ ppm: 1.76 (m, 2 H), 2.30–3.10 (m, 12 H), 3.35 (s, 3 H), 3.40 (s, 3 H), 3.74 (m, 1 H), 3.20 (br., 1 H), 5.26 (s, 1 H), 7.29 (m, 5 H).

IR KBr ν max (cm$^{-1}$): 3470, 2920, 2830, 2800, 1700, 1640, 1610, 1490, 1430, 1370, 1300, 1205, 800, 760.

Furthermore, 0.98 g of this pyrimidinedione derivative was treated with a hydrochloric acid/methanol solution in an ordinary manner to prepare 0.76 g of crystalline 1,3-dimethyl-6-[4-(2-hydroxy-4-phenyl-butyl)piperazin-1-yl]-2,4(1H,3H)-pyrimidinedione.hydrochloride (Compound 1).

Analytical results of the obtained Compound 1

Melting point: 180° to 183° C.

IR KBr ν max (cm$^{-1}$): 3300, 2920, 2450, 1705, 1640, 1610, 1490, 1440, 800, 750.

Values of elemental analysis (as $C_{20}H_{28}N_4O_3 \cdot HCl$):
Calcd. (%): C 58.74; H 7.15; N 13.70; Cl 8.67; Found (%): C 58.38; H 7.44; N 13.61; Cl 8.54.

EXAMPLE 2

Preparation of
1,3-Dimethyl-6-[2-(2-hydroxy-4-phenylbutylamino)ethylamino]-2,4(1H,3H)-pyrimidinedione.hydrochloride
(Compound 2)

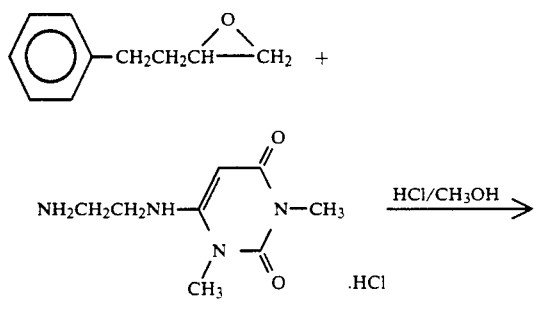

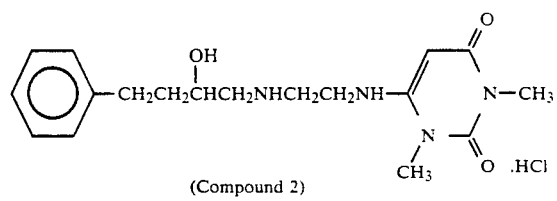

(Compound 2)

0.98 g of 1,2-epoxy-4-phenylbutane obtained in the section (2) in Example 1, 3.3 g of 1,3-dimethyl-6-(2-aminoethylamino)-2,4(1 H,3 H)-pyrimidinedione.hydrochloride and 3 ml of triethylamine were suspended in 50 ml of ethanol, and the suspension was then refluxed for 3 hours. The solvent was distilled off under reduced pressure from the resulting reaction solution, and 100 ml of chloroform was added to the residue. The resulting solution was washed with water and then dried over anhydrous sodium sulfate, and the solvent was distilled off to obtain a residue. This residue was then purified through a silica gel column chromatograph (chloroform/methanol = 50/1 to 5/1 in volume ratio), thereby obtaining 0.49 g of white crystals of 1,3-dimethyl-6-[2-(2-hydroxy-4-phenylbutylamino)ethylamino]-2,4(1H,3H)pyrimidinedione.

Analytical results of the obtained pyrimidinedione derivative

Melting point: 98° to 101° C.

NMR (CDCl₃) δ ppm: 1.76 (m, 2 H), 2.32 (br., 2 H), 2.30–3.28 (m, 8 H), 3.29 (s, 3 H), 3.36 (s, 3 H), 3.66 (m, 1 H), 4.78 (s, 1 H), 5.60 (br., 1 H), 7.24 (m, 5 H).

IR KBr ν max (cm⁻¹): 3400, 3300, 2920, 1690, 1610, 1550, 1455, 1435.

Furthermore, 0.45 g of this pyrimidinedione derivative was treated with a hydrochloric acid/methanol solution in an ordinary manner to prepare 0.46 g of crystals of 1,3-dimethyl-6-[2-(2-hydroxy-4-phenylbutylamino)ethylamino]-2,4(1 H,3 H)-pyrimidinedione.hydrochloride (Compound 2).

Analytical results of the obtained Compound 2
Melting point: 211° to 213° C.

IR KBr ν max (cm⁻¹): 3310, 1700, 1640, 1615, 1563, 1480, 1440, 1250.

Values of elemental analysis (as $C_{20}H_{29}N_5O_5 \cdot HCl$):
Calcd. (%): C 56.46; H 7.11; N 14.63; Cl 9.26; Found (%): C 55.97; H 6.99; N 14.53; Cl 9.05.

EXAMPLE 3

Preparation of
1,3-Dimethyl-6-[4-(2-fluoro-4-phenylbutyl)piperazin-1-yl]-2,4(1 H,3 H)-pyrimidinedione.hydrochloride
(Compound 3)

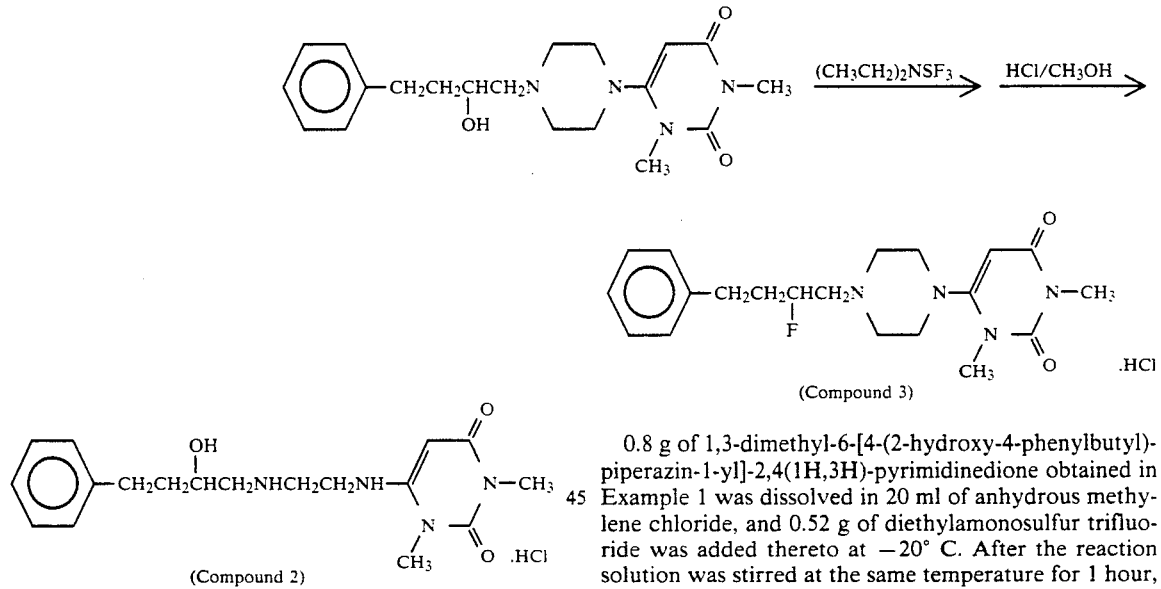

(Compound 3)

0.8 g of 1,3-dimethyl-6-[4-(2-hydroxy-4-phenylbutyl)-piperazin-1-yl]-2,4(1H,3H)-pyrimidinedione obtained in Example 1 was dissolved in 20 ml of anhydrous methylene chloride, and 0.52 g of diethylamonosulfur trifluoride was added thereto at −20° C. After the reaction solution was stirred at the same temperature for 1 hour, an aqueous saturated sodium hydrogencarbonate solution was added to the reaction solution, and after stirring, the resulting methylene chloride layer was separated. 50 ml of methylene chloride was further added to the obtained organic layer, and after washing with water, the solution was dried over anhydrous sodium sulfate. Afterward, the solvent was distilled off under reduced pressure, and the resulting residue was then purified through a silica gel column chromatograph (chloroform/methanol = 50/1 in volume ratio), thereby obtaining 0.38 g of white crystals of 1,3-dimethyl-6-[4-(2-fluoro-4-phenylbutyl)piperazin-1-yl]-2,4(1 H,3 H)-pyrimidinedione.

Analytical results of the obtained pyrimidinedione derivative crystals

Melting point: 114° to 115.5° C.

IR KBr ν max (cm⁻¹): 3080, 2935, 2800, 1690, 1630, 1600, 1480, 1430, 1370, 1200, 1140.

Furthermore, 0.35 g of this pyrimidinedione derivative was treated with a hydrochloric acid/methanol solution in an ordinary manner to prepare 0.37 g of crystals of 1,3-dimethyl-6-[4-(2-fluoro-4-phenylbutyl)-piperazin-1-yl]-2,4(1H,3H)-pyrimidinedione.hydrochloride (Compound 3).

Analytical results of the obtained Compound 3
Melting point: 227° to 229° C.

IR KBr ν max (cm$^{-1}$): 2940, 2340, 1690, 1645, 1620, 1490, 1435, 1390, 1205.

Values of elemental analysis (as $C_{20}H_{27}N_4O_2F \cdot HCl$): Calcd. (%): C 58.46; H 6.87; N 13.63; Cl 8.63; Found (%): C 57.83; H 7.02; N 13.41; Cl 9.14.

EXAMPLE 4

Preparation of 1,3-Dimethyl-6-[4-(2-ethoxycarbonyl-2-phenylethyl)-piperazin-1-yl]-2,4(1H,3H)-pyrimidinedione.hydrochloride (Compound 4)

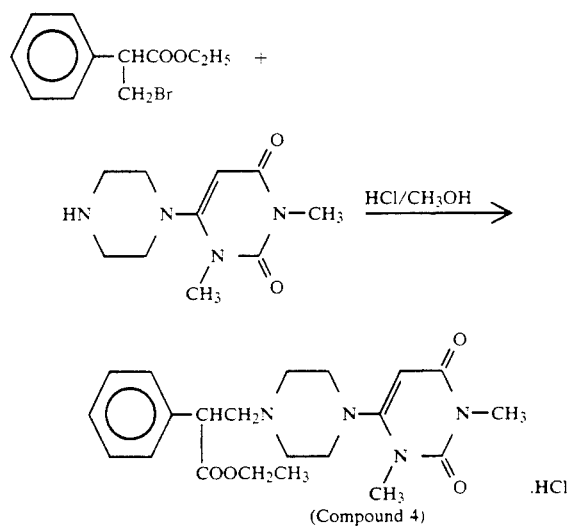

(Compound 4)

8.1 g of α-phenyl-β-bromopropionic acid and 1,3-dimethyl-6-(1-piperazinyl)-2,4(1H,3H)-pyrimidinedione were dissolved in 90 ml of dioxane, and the solution was stirred at 90° C. for 30 minutes. 12 ml of triethylamine was added to this solution, followed by stirring at 90° C. for 1 hour. Afterward, 60 ml of ethanol was added, and the solution was then heated under reflux for 3 hours. The solvent was distilled off from the reaction solution under reduced pressure, and the resulting residue was then dissolved in chloroform. The obtained solution was washed with water and then dried over anhydrous sodium sulfate. Afterward, the solvent was distilled off under reduced pressure, and the resulting residue was then purified through a silica gel column chromatograph (chloroform), thereby obtaining 4.5 g of 1,3-dimethyl-6-[4-(2-ethoxycarbonyl-2-phenylethyl)piperazin-1-yl]-2,4(1H,3H)-pyrimidinedione.

Analytical results of the obtained pyrimidinedione derivative

IR KBr ν max (cm$^{-1}$): 3440, 2960, 2840, 1730, 1690, 1660, 1600, 1470, 1380, 1300, 1260, 1200.

NMR (CDCl$_3$) δ ppm: 1.2 (t, 2 H), 2.4–3.2 (m, 10 H), 3.4 (s, 3 H), 3.45 (s, 3 H), 3.9 (m, 1 H), 5.2 (s, 1 H), 7.3 (s, 5 H).

Furthermore, 1 g of this pyrimidinedione derivative was treated with a hydrochloric acid/methanol solution in an ordinary manner to prepare 0.9 g of 1,3-dimethyl-6-[4-(2-ethoxycarbonyl-2-phenylethyl)piperazin-1-yl]-2,4(1H,3H)-pyrimidinedione.hydrochloride (Compound 4).

Analytical results of the obtained Compound 4
Melting point: Amorphous.

Values of elemental analysis (as $C_{21}H_{28}N_4O_4 \cdot HCl$): Calcd. (%): C 57.73; H 6.69; N 12.82; Cl 8.11; Found (%): C 57.43; H 6.22; N 13.11; Cl 8.51.

EXAMPLE 5

Preparation of 1,3-Dimethyl-6-[4-(3-hydroxy-2-phenylpropyl)piperazin-1-yl]-2,4(1H,3H)-pyrimidinedione.oxalate (Compound 5)

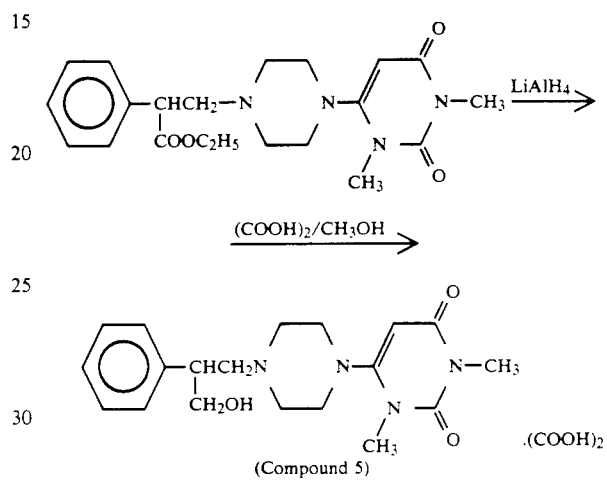

(Compound 5)

1.3 g of 1,3-dimethyl-6-[4-(2-ethoxycarbonyl-2-phenylethyl)piperazin-1-yl]-2,4(1H,3H)-pyrimidinedione obtained in Example 4 was dissolved in 50 ml of tetrahydrofuran, and while the resulting solution was cooled to $-20°$ C., 1.1 g of aluminum lithium hydride was divided into several portions and then added thereto separately. After stirring at $-10°$ C. for 1 hour, 0.7 ml of water was added to the solution at the same temperature. The reaction solution was stirred for 2 or 3 hours, and 3 g of anhydrous sodium sulfate was added thereto, followed by allowing the solution to stand overnight. Afterward, insolubles were removed from the solution by filtration, and the filtrate was concentrated and the resulting residue was then dissolved in ethyl acetate. The obtained solution was washed with water and then dried over anhydrous sodium sulfate, and the solvent was distilled off under reduced pressure. The resulting residue was purified through a silica gel column chromatograph (chloroform/methanol=100/1 to 30/1 in volume ratio), thereby obtaining 0.5 g of oily 1,3-dimethyl-6-[4-(3-hydroxy-2-phenylpropyl)piperazin-1-yl]-2,4(1H,3H)-pyrimidinedione.

Analytical results of the obtained pyrimidinedione derivative

NMR (CDCl$_3$) δ ppm: 2.4–3.1 (m, 11 H), 3.30 (s, 3 H), 3.35 (s, 3 H), 3.7–4.0 (m, 2 H), 5.0 (br., 1 H), 5.2 (s, 1 H), 7.2 (s, 5 H).

Furthermore, 0.45 g of this pyrimidinedione derivative was treated with an oxalic acid/methanol solution in an ordinary manner to prepare 0.3 g of crystals of 1,3-dimethyl-6-[4-(3-hydroxy-2-phenylpropyl)piperazine-1-yl]-2,4(1H,3H)-pyrimidinedione.oxalate (Compound 5).

Analytical results of the obtained Compound 5
Melting point: 128° to 130° C.

IR KBr ν max (cm$^{-1}$): 3200, 2940, 2890, 2820, 1680, 1630, 1600, 1490, 1430, 1360, 1200, 1130, 1030.

Values of elemental analysis (as $C_{19}H_{26}N_4O_3 \cdot (COOH)_2 \cdot H_2O$): Calcd. (%): C. 54.07; H 6.48; N 11.76; Found (%): C. 54.02; H 6.56; N 12.01.

EXAMPLE 6

Preparation of 1,3-Dimethyl-6-[4-(1-ethoxycarbonyl-2-phenylethyl)piperazine-1-yl]-2,4(1H,3H)-pyrimidinedione.hydrochloride (Compound 6)

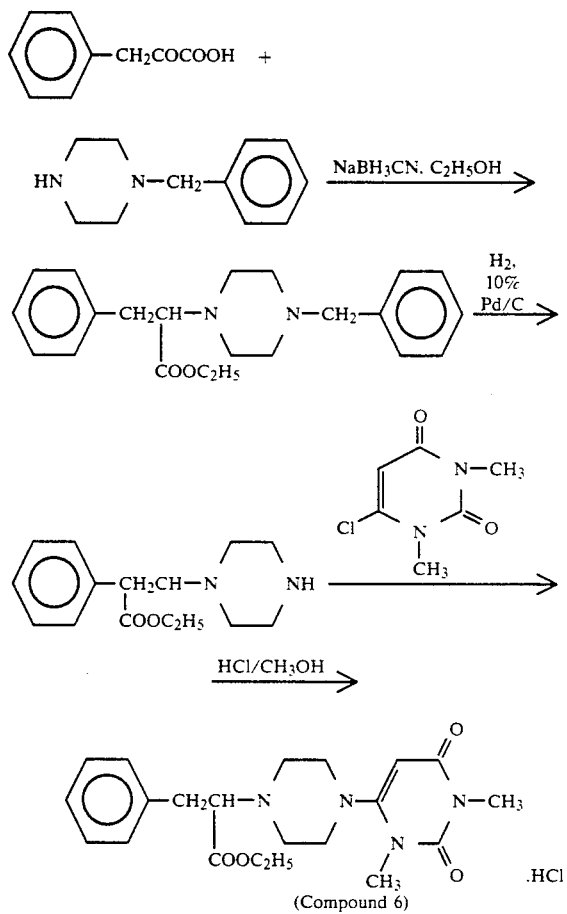

(1) Preparation of 1-benzyl-4-(1-ethoxycarbonyl-2-phenylethyl)piperazine 14.2 g of N-benzylpiperazine was dissolved in 50 ml of methanol, and 20 ml of a methanol solution containing 13.2 g of phenylpyruvic acid was added dropwise thereto. The solution was then stirred at room temperature for 10 minutes, and 10 ml of a 15% HCl/methanol (weight ratio) was added dropwise to the solution slowly, followed by stirring for 1.5 hours. Afterward, 30 ml of methanol containing 9.2 g of sodium borocyanohydride was added dropwise to the resulting reaction solution slowly over about 6 hours under ice cooling, followed by allowing the solution to stand overnight. Next, the solvent was distilled off from the reaction solution, and the resulting residue was dissolved in chloroform. The thus obtained solution was washed with a dilute aqueous sodium hydroxide solution and then with water, and the solvent was distilled off therefrom. The resulting residue was dissolved in 600 ml of ethanol, and 12 ml of concentrated sulfuric acid was added thereto and the solution was then heated under reflux for 4 hours. Next, the solvent was distilled off under reduced pressure from the reaction solution, and 200 ml of ice water and 200 ml of chloroform were added thereto. Moreover, an aqueous saturated sodium hydrogencarbonate solution was added to the solution to make an aqueous layer alkaline. After stirring, the organic layer was separated from the solution, washed with water, and then concentrated under reduced pressure. The resulting residue was purified through a silica gel column chromatograph (chloroform), thereby obtaining 7.6 g of 1-benzyl-4-(1-ethoxycarbonyl-2-phenylethyl)-piperazine in an oily state.

Analytical results of the obtained piperazine derivative

NMR (CDCl$_3$) δ ppm: 1.1 (t, 3 H), 2.4–2.9 (m, 8 H), 2.9–3.1 (m, 2 H), 3.3–3.5 (m, 1 H), 3.5 (s, 2 H), 4.0 (q. 2 H), 7.2 (s, 5 H), 7.3 (s, 5 H).

IR neat ν max (cm$^{-1}$): 3020, 2940, 2810, 1730, 1600, 1580, 1500, 1450, 1350, 1300, 1200, 1160, 1010.

(2) Preparation of 1-(1-ethoxycarbonyl-2-phenylethyl)piperazine 6.2 g of 1-benzyl-4-(1-ethoxycarbonyl-2-phenylethyl)piperazine obtained in the above-mentioned section (1) was dissolved in a mixed solvent of 100 ml of methanol and 100 ml of acetic acid, and 50 ml of a 13% HCl/methanol solution and 0.4 g of a 10% Pd/C. solution were added to the resulting solution. Afterward, hydrogenation was carried out at ordinary pressure After the reaction, the solvent was distilled off from the reaction solution, and the resulting residue was then dissolved in chloroform. The resulting solution was washed with an aqueous saturated sodium hydrogencarbonate solution and further with water. The solvent was distilled off from the water-washed organic layer under reduced pressure to obtain 4.5 g of 1-(1-ethoxycarbonyl-2-phenylethyl)piperazine in an oily state.

Analytical results of the obtained piperazine derivative

IR neat ν max (cm$^{-1}$): 3300, 2940, 2820, 1730, 1600, 1500, 1450, 1200, 1160, 1030.

NMR (CDCl$_3$) δ ppm: 1.2 (t, 3 H), 1.9 (br., 1 H), 2.5–3.2 (m, 10 H), 3.3–3.6 (m, 1 H), 4.2 (q. 2 H), 7.3 (s, 5 H).

(3) Preparation of 1,3-dimethyl-6-[4-(1-ethoxycarbonyl-2-phenylethyl)piperazin-1-yl]-2,4(1H,3H)-pyrimidinedione.hydrochloride (Compound 6)

4.2 g of 1-(1-ethoxycarbonyl-2-phenylethyl)piperazine obtained in the above-mentioned section (2), 3.5 g of 6-chloro-1,3-dimethyl-2,4(1H,3H)-pyrimidinedione and 4.2 ml of triethylamine were dissolved in 100 ml of dioxane, and the solution was heated with stirring at a temperature of from 80° to 90° C. for 8 hours. After the reaction, the solvent was distilled off from the reaction solution, and the resulting residue was dissolved in chloroform. The thus obtained chloroform solution was washed with water and then dried over anhydrous sodium sulfate, and the solvent was further distilled off under reduced pressure. The resulting concentrate was purified through a silica gel column chromatograph (chloroform/methanol=100/1 in volume ratio), thereby obtaining 3.3 g of 1,3-dimethyl-6-[4-(1-ethoxycarbonyl-2-phenylethyl)piperazin-1-yl]-2,4(1H,3H)-pyrimidinedione in an oily state.

Analytical results of the obtained pyrimidinedione derivative

IR nujol ν max (cm$^{-1}$): 2920, 2850, 1720, 1690, 1650, 1600, 1450, 1380, 1200, 1170, 1000.

NMR (CDCl$_3$) δ ppm: 1.2 (t, 3 H), 2.7–3.2 (m, 10 H), 3.35 (s, 3 H), 3.4 (s, 3 H), 3.3–3.6 (m, 1 H), 4.1 (q, 2 H), 5.2 (2, 1 H), 7.3 (s, 5 H).

Furthermore, 0.5 g of this pyrimidinedione derivative was treated with a hydrochloric acid/methanol solution in an ordinary manner to prepare 0.3 g of crystals of 1,3-dimethyl-6-[4-(1-ethoxycarbonyl-2-phenylethyl)-piperazin-1-yl]-2,4(1H,3H)-pyrimidinedione.hydrochloride (Compound 6).

Analytical results of the obtained Compound 6

Values of elemental analysis (as C$_{21}$H$_{28}$N$_4$O$_4$.HCl): Calcd. (%) C. 57.73; H 6.69; N 12.82; Cl 8.11; Found (%): C. 57.64; H 7.09; N 12.85; Cl 7.80.

EXAMPLE 7

Preparation of 1,3-Dimethyl-6-[4-(1-benzyl-2-hydroxyethyl)piperazin-1-yl]-2,4(1H,3H)-pyrimidinedione.oxalate (Compound 7)

Analytical results of the obtained pyrimidinedione derivative

IR KBr ν max (cm$^{-1}$): 3400, 2840, 1690, 1640, 1590, 1470, 1430, 1360, 1200, 1030, 800.

NMR (CDCl$_3$) δ ppm: 2.2–3.1 (m, 11 H), 3.3 (s, 3 H), 3.35 (s, 3 H), 3.2–3.6 (m, 2 H), 5.2 (s, 1 H), 7.0–7.3 (m, 5 H).

Furthermore, 0.5 g of this pyrimidinedione derivative was treated with an oxalic acid/methanol solution in an ordinary manner to prepare 0.3 g of crystals of 1,3-dimethyl-6-[4-(1-benzyl-2-hydroxyethyl)piperazin-1-yl]-2,4(1H,3 H)-pyrimidinedione.oxalate (Compound 7).

Analytical results of the obtained Compound 7

Melting point: 175° to 177° C.

NMR (DMSO-d$_6$) δ ppm: 2.6–3.4 (m, 11 H), 3.1 (s, 3 H), 3.3 (s, 3 H), 3.4–3.6 (m, 2 H), 5.2 (s, 1 H), 7.3 (s, 5 H).

Values of elemental analysis (as C$_{19}$H$_{26}$N$_4$O$_3$.-(COOH)$_2$.H$_2$O): Calcd. (%): C. 54.07; H 6.48; N 12.01;

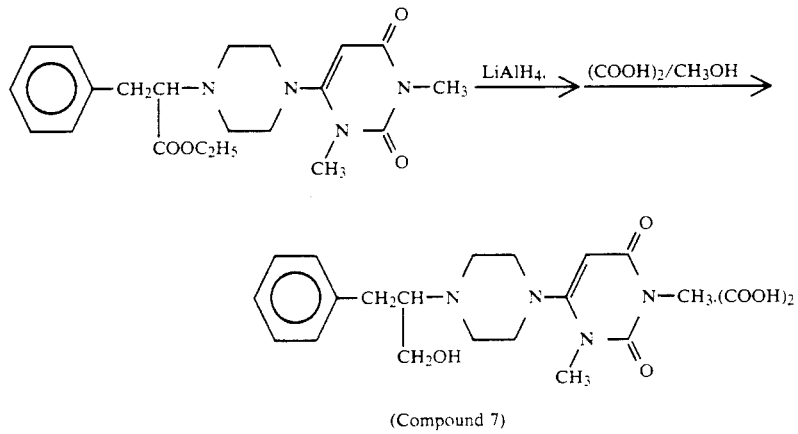

(Compound 7)

2 g of 1,3-dimethyl-6-[4-(1-ethoxycarbonyl-2-phenylethyl)piperazin-1-yl]-2,4(1H,3H)-pyrimidinedione obtained in Example 6 was treated in accordance with the procedure of Example 5 to obtain 1 g of white crystals of 1,3-dimethyl-6-[4-(1-benzyl-2-hydroxyethyl)piperazin-1-yl]-2,4(1H,3H)-pyrimidinedione.

Found (%): C. 53.83; H 6.55; N 12.03.

EXAMPLE 8

Preparation of 1,3-Dimethyl-6-[4-(1-ethoxycarbonyl-3-phenylpropyl)-piperazin-1-yl]-2,4(1H,3H)-pyrimidinedione.oxalate (Compound 8)

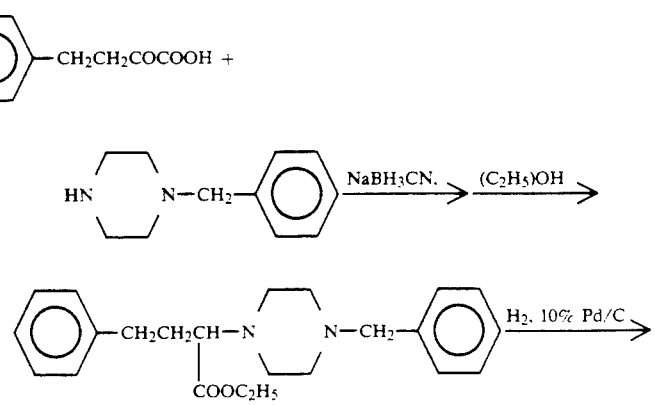

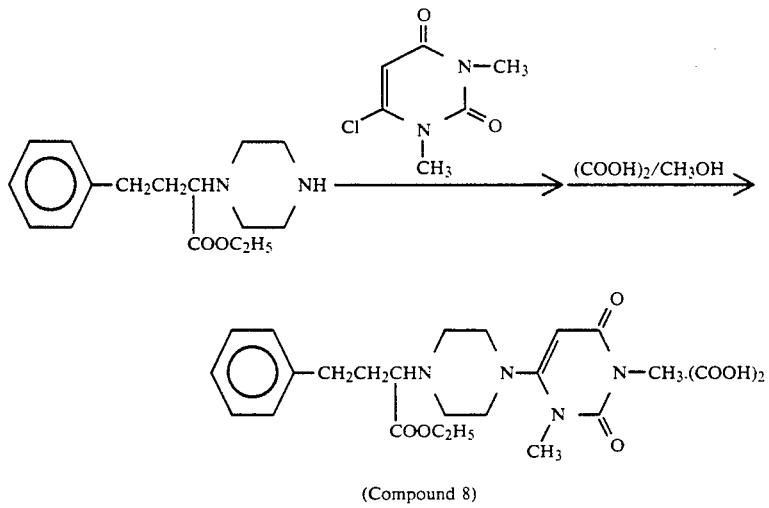

(Compound 8)

(1) Preparation of 1-benzyl-4-(1-ethoxycarbonyl-3-phenylpropyl)piperazine 17.6 g of N-benzylpiperazine and 17.8 g of benzylpyruvic acid were treated in accordance with the same procedure as in the section (1) of Example 6 to obtain 13.0 g of 1-benzyl-4-(1-ethoxycarbonyl-3-phenylpropyl)piperazine.

Analytical results of the obtained piperazine derivative

NMR (CDCl$_3$) δ ppm: 1.2 (t, 3 H, 2.0 (m, 2 H), 2.2-2.9 (m, 10 H), 3.1 (t, 1 H), 3.5 (s, 2 H, 4.1 (q, 2 H), 7.1 (s, 5 H), 7.2 (s, 5 H).

(2) Preparation of 1-(1-ethoxycarbonyl-3-phenylpropyl)piperazine 4.5 g of 1-benzyl-4-(1-ethoxycarbonyl-3-phenylpropyl)piperazine obtained in the above-mentioned section (1) was treated in accordance with the same procedure as in the section (2) of Example 6 to obtain 2.8 g of 1-(1-ethoxycarbonyl-3-phenylpropyl)piperazine in an oily state.

Analytical results of the obtained piperazine derivative

IR neat ν max (cm$^{-1}$): 3300, 2920, 2810, 1720, 1660, 1450, 1150, 1020.

NMR (CDCl$_3$) δ ppm: 1.2 (t, 3 H), 2.4-3.8 (m, 11 H), 4.1 (q, 2 H), 7.2 (s, 5 H).

(3) Preparation of 1,3-dimethyl-6-[4-(1-ethoxycarbonyl-3-phenylpropyl)piperazin-1-yl]-2,4(1H,3H)-pyrimidinedione.oxalate (Compound 8)

2.6 g of 1-(1-ethoxycarbonyl-3-phenylpropyl)piperazine obtained in the above-mentioned section (2), 2.6 g of 6-chloro-1,3-dimethyl-2,4(1H,3H)-pyrimidinedione and 2.5 g of triethylamine were dissolved in 20 ml of dioxane, and the solution was then heated with stirring at a temperature of from 80 to 90° C. for 2 hours. After the reaction, the solvent was distilled off from the reaction solution, and the resulting residue was dissolved in chloroform. The thus obtained chloroform solution was washed with water and then dried over anhydrous sodium sulfate, and the solvent was further distilled off under reduced pressure. The resulting concentrate was purified through a silica gel column chromatograph (chloroform), thereby obtaining 2.9 g of 1,3-dimethyl-6-[4-(1-ethoxycarbonyl-3-phenylpropyl)piperazin-1-yl]-2,4(1H,3H)-pyrimidinedione in an oily state.

Analytical results of the obtained pyrimidinedione derivative

IR neat ν max (cm$^{-1}$): 2930, 2830, 1720, 1690, 1640, 1600, 1480, 1430, 1370, 1160, 1020, 990.

NMR (CDCl$_3$) δ ppm: 1.3 (t, 3 H), 1.9-2.2 (m, 2 H), 2.4-3.3 (m, 11 H), 3.3 (s, 3 H), 3.35 (s, 3 H), 4.2 (q, 2 H), 5.2 (s, 1 H), 7.2 (s, 5 H).

Furthermore, 0.55 g of this pyrimidinedione derivative was treated with an oxalic acid/methanol solution in an ordinary manner to prepare 0.3 g of crystals of 1,3-dimethyl-6-[4-(1-ethoxycarbonyl-3-phenylpropyl)-piperazin-1-yl]-2,4(1H,3H)-pyrimidinedione.oxalate (Compound 8).

Analytical results of the obtained Compound 8

Values of elemental analysis (as C$_{22}$H$_{30}$N$_4$O$_4$.(COOH)$_2$.2H$_2$O): Calcd (%) C. 53.32; H 6.71; N 10.36; Found (%): C. 53.44; H 6.38; N 10.15.

NMR (DMSO-d$_6$) δ ppm: 1.3 (t, 3 H), 1.9-2.1 (m, 2 H), 2.5-3.3 (m, 11 H), 3.15 (s, 3 H), 3.3 (s, 3 H), 4.1 (m, 2 H), 5.2 (s, 1 H), 7.25 (s, 5 H).

EXAMPLE 9

Preparation of 1,3-Dimethyl-6-[4-(1-hydroxy-4-phenylbutan-2-yl)piperazin-1-yl]-2,4(1H,3H)-pyrimidinedione.oxalate (Compound 9)

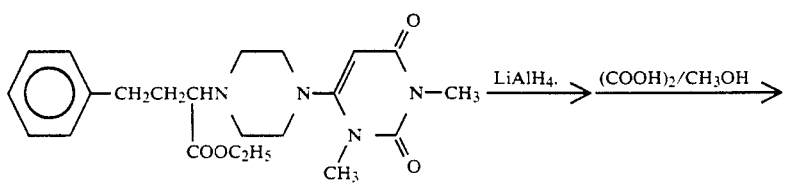

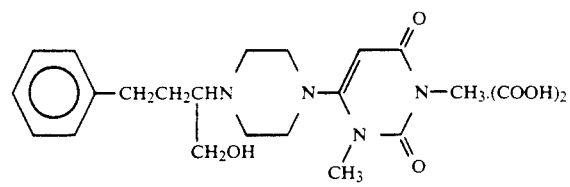

(Compound 9)

1 g of 1,3-dimethyl-6-[4-(1-ethoxycarbonyl-3-phenylpropyl)piperazin-1-yl]-2,4(1H,3H)-pyrimidinedione obtained in Example 8 was treated in accordance with the same procedure as in Example 5 to obtain 0.45 g of 1,3-dimethyl-6-[4-(1-hydroxy-4-phenylbutan-2-yl)piperazin-1-yl]-2,4(1H,3H)-pyrimidinedione in an oily state.

Analytical results of the obtained pyrimidinedione derivative

IR nujol $\nu$ max (cm$^{-1}$): 2900, 2830, 1680, 1640, 1460, 1370, 1030.

NMR (CDCl$_3$) $\delta$ ppm: 1.8–2.1 (m, 2 H), 2.4–3.2 (m, 11 H), 3.1 (s, 3 H), 3.2 (s, 3 H), 3.8 (m, 2 H), 5.1 (s, 1 H), 7.2 (s, 5 H).

Furthermore, 0.25 g of this pyrimidinedione derivative was treated with an oxalic acid/methanol solution in an ordinary manner to prepare 0.1 g of crystals of 1,3-dimethyl-6-[4-(1-hydroxy-4-phenylbutan-2-yl)piperazin-1-yl]-2,4(1H,3H)-pyrimidinedione.oxalate (Compound 9).

Analytical results of the obtained Compound 9

Melting point: 143° to 146° C.

NMR (DMSO-d$_6$) $\delta$ ppm: 1.7–2.0 (m, 2 H), 2.4–3.4 (m, 11 H), 3.1 (s, 3 H), 3.3 (s, 3 H), 3.7 (m, 2 H), 5.2 (s, 1 H), 7.3 (s, 5 H).

Values of elemental analysis (as C$_{20}$H$_{28}$N$_4$O$_3$.(COOH)$_2 \frac{1}{2}$H$_2$O): Calcd. (%): C. 56.04; H 6.63; N 11.88; Found (%): C. 56.68; H 6.86; N 11.86.

EXAMPLE 10

Preparation of 1,3-Dimethyl-6-[4-(3-[4-chlorophenoxy]-2-(2-methoxyethoxy)propyl)piperazin-1-yl]-2,4(1H,3H)-pyrimidinedione.hydrochloride (Compound 10)

dinedione was dissolved in 30 ml of dimethylformamide, and 0.25 g of sodium hydride (60% and oily) was further added thereto. The solution was stirred at room temperature for 30 minutes, and 0.85 ml of methoxyethyl bromide was then added thereto. After stirring for 3 days, 100 ml of chloroform was added to the reaction solution This solution was washed with water and then dried with anhydrous magnesium sulfate, and the solvent was distilled off under reduced pressure. The resulting residue was purified through a silica gel column chromatograph (chloroform/methanol=30/1 in volume ratio), thereby obtaining 2.0 g of 1,3-dimethyl-6-[4-(3-[4-chlorophenoxy]-2-(2-methoxyethoxy)propyl)piperazin-1-yl]-2,4(1H,3H)-pyrimidinedione.

Analytical results of the obtained pyrimidinedione derivative

NMR (CDCl$_3$) $\delta$ ppm: 2.5–3.1 (m, 10 H), 3.3 (s, 3 H), 3.36 (s, 3 H), 3.2–4.2 (m, 7 H), 5.26 (s, 1 H), 6.86 (d, 2 H), 7.3 (d, 2 H).

Furthermore, 2 g of this pyrimidinedione derivative was treated with a hydrochloric acid/methanol solution in an ordinary manner to prepare 0.8 g of crystals of 1,3-dimethyl-6-[4-(3-[4-chlorophenoxy]-2-(2-methoxyethoxy)propyl)piperazin-1-yl]-2,4(1H,3H)-pyrimidinedione.hydrochloride (Compound 10).

Analytical results of the obtained Compound 10

Melting point: 182° to 184° C.

Values of elemental analysis (as C$_{21}$H$_{31}$N$_4$O$_3$Cl.HCl) Calcd. (%): C 51.32; H 6.56; N 11.40; Cl 14.43; Found (%): C 51.88; H 6.35; N 11.48; Cl 14.28.

EXAMPLE 11

Preparation of 1,3-dimethyl-6-[2-(4-[4-fluoroben-

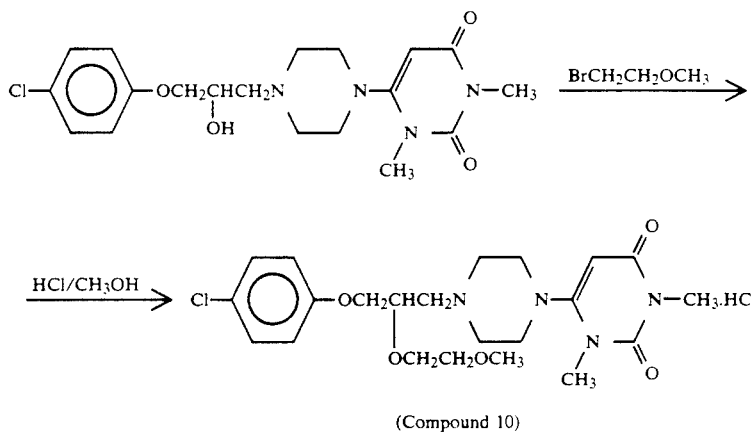

(Compound 10)

1.0 g of 1,3-dimethyl-6-[4-(3-[4-chlorophenoxy]-2-hydroxypropyl)piperazin-1-yl]-2,4(1H,3H)-pyrimizoyl]-piperide-1-yl)ethylamino]-2,4-(1H,3H)-pyrimidinedione.oxalate (Compound 11)

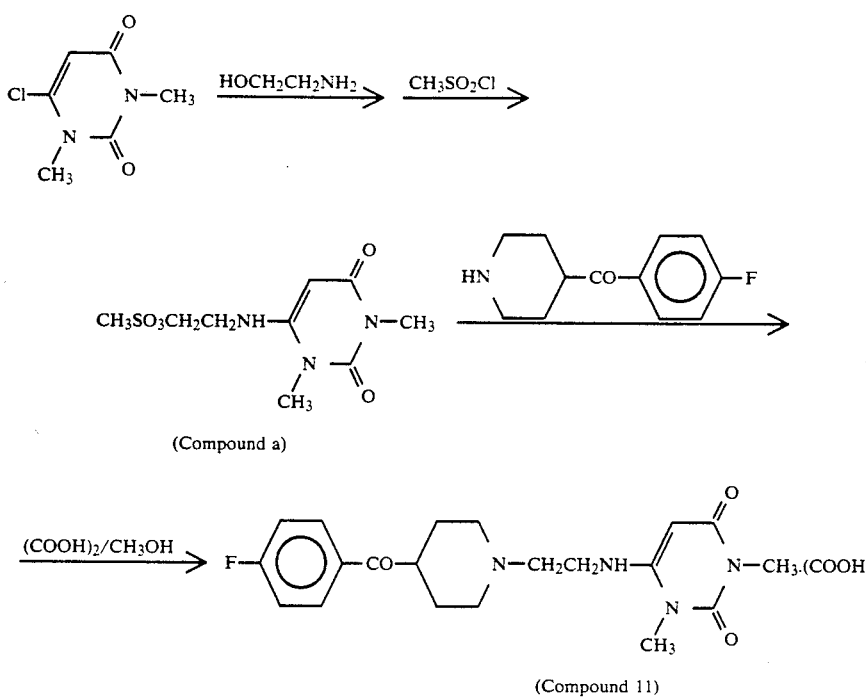

(Compound a)

(Compound 11)

(1) Preparation of 1,3-dimethyl-6-(2-methanesulfonyloxyethylamino)-2,4(1H,3H)-pyrimidinedione (Compound a)

52.4 g of 6-chloro-1,3-dimethyl-2,4(1H,3H)-pyrimidinedione was dissolved in 280 ml of pyridine, and 45.5 g of triethylamine and 21.3 g of aminoethanol were further added thereto. Afterward, the solution was heated with stirring at 90° C. for 4 hours. The reaction solution was ice-cooled so as to maintain its internal temperature at a level of from 0° to 4° C., and 55.8 g of methanesulfonyl chloride was added dropwise thereto. The solution was then stirred at the same temperature for 3 hours, and 1.2 liters of methanol was added thereto, followed by stirring for 2 hours. Crystals precipitated in this reaction solution were collected by filtration and further recrystallized from 3.5 liters of methanol to obtain 70.0 g of crystalline 1,3-dimethyl-6-(2-methanesulfonyloxyethylamino)-2,4-(1H,3H)-pyrimidinedione (Compound a).

Analytical results of the Compound a

Melting point: 169° to 170° C.

NMR (CDCl$_3$) δ ppm: 3.09 (s, 3 H), 3.19 (s, 3 H), 3.28 (s, 3 H), 3.35–3.50 (m, 2 H), 4.30 (t, 2 H), 4.81 (s, 1 H), 6.93 (t, 1 H).

(2) Preparation of 1,3-dimethyl-6-[2-(4-[4fluorobenzoyl]piperide-1-yl)ethylamino)-2,4(1H,3H)-pyrimidinedione.oxalate (Compound 11)

1 g of 1,3-dimethyl-6-(2-methanesulfonyloxyethylamino)-2,4(1H,3 H)-pyrimidinedione (Compound a) obtained in the above-mentioned section (1) and 0.42 g of 4-(4-fluorobenzoyl)piperide were mixed and then heated at 100° C. for 30 minutes. After standing for cooling, 100 ml of chloroform was added to the solution, and the thus obtained chloroform solution was washed with a dilute aqueous sodium hydroxide solution and then with water, and the solvent was distilled off therefrom under reduced pressure. The resulting residue was purified through a silica gel column chromatograph (chloroform/methanol=40/1 in volume ratio), thereby obtaining 0.4 g of 1,3-dimethyl-6-[2-(4-[4-fluorobenzoyl]piperide-1-yl)ethylamino]-2,4(1H,3H)-pyrimidinedione.

Analytical results of the obtained pyrimidinedione derivative

NMR (CDCl$_3$) δ ppm: 2.0–2.2 (m, 5 H), 3.2 (m, 2 H), 2.9–3.1 (m, 6 H), 3.36 (s, 3 H), 3.40 (s, 3 H), 5.12 (s, 1 H), 7.49 (d, 2 H), 7.88 (d, 2 H).

Furthermore, 0.35 g of this pyrimidinedione derivative was treated with an oxalic acid/methanol solution in an ordinary manner to prepare 0.2 g of 1,3-dimethyl-6-[ 2-(4-[4-fluorobenzoyl]piperide-1-yl)ethylamino]-2,4(1H,3H)-pyrimidinedione.oxalate (Compound 11).

Analytical results of the obtained Compound 11

Melting point: 117° to 118° C.

Values of elemental analysis (as C$_{20}$H$_{26}$N$_4$O$_3$F.2-(COOH)$_2$.H$_2$O) Calcd. (%): C. 49.06; H 5.49; N 9.54; Found (%): C. 49.11; H 5.81; N 9.56.

IR KBr ν max (cm$^{-1}$): 2900, 1710, 1680, 1640, 1620, 1170, 850.

EXAMPLE 12

Preparation of 1,3-Dimethyl-6-[2-(N-[2-hydroxyethyl]-3-(4-nitrophenyl)butylamino)ethylamino]-2,4(1H,3H)-pyrimidinedione.fumarate (Compound 12)

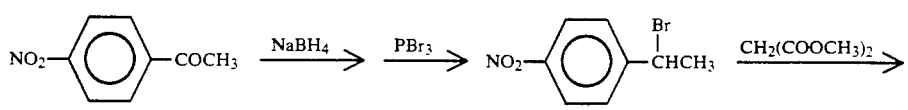

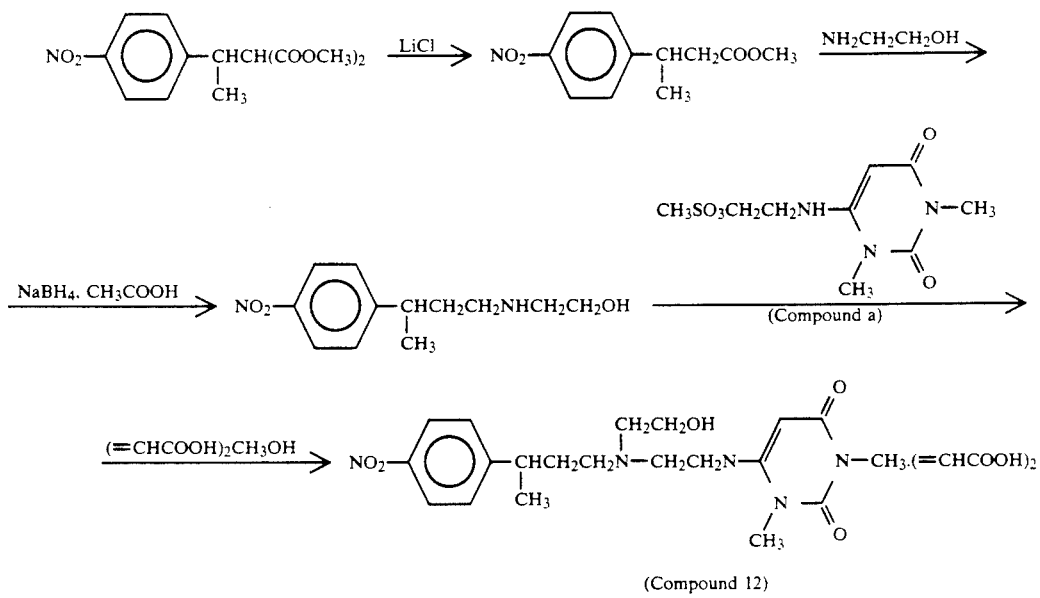

(1) Preparation of 1-(4-nitrophenyl)ethyl bromide 6.0 g of p-nitroacetophenone was dissolved in 100 ml of ethanol, and 0.75 g of sodium borohydride was added thereto under ice cooling. Afterward, the reaction solution was stirred at room temperature for 2 hours, and 1 ml of 0.1N hydrochloric acid was added thereto so as to bring the reaction to an end. This reaction mixture was concentrated under reduced pressure, and 100 ml of 0.5N hydrochloric acid was added to the resulting residue and extraction was then carried out twice with 50 ml of ether. The resulting ether layers were joined together, washed with water, and then dried over anhydrous sodium sulfate, and the solvent was distilled off. Afterward, the resulting residue was dissolved in 100 ml of methylene chloride. 7.2 g of phosphorus tribromide was added dropwise to the solution under ice cooling, followed by stirring at room temperature for 10 hours. Next, an aqueous potassium carbonate solution was added to the reaction solution to neutralize the same, and the resulting methylene chloride layer was separated, washed with water, and then dried over anhydrous sodium sulfate. Afterward, the solvent was distilled off under reduced pressure, and the resulting residue was purified through a silica gel column chromatograph (chloroform/hexane=2/1 in volume ratio), thereby obtaining 3.5 g of oily 1-(4-nitrophenyl)ethyl bromide.

Analytical results of the obtained bromide derivative

NMR (CDCl$_3$) δ ppm: 2.06 (d, 3 H), 5.23 (q, 1 H), 7.60 (d, 2 H), 8.20 (d, 2 H).

(2) Preparation of dimethyl 1-(4-nitrophenyl)ethylmalonate 1.18 g of sodium hydride (60% and oily) was suspended in 20 ml of dimethyl sulfoxide, and 3.9 g of dimethyl malonate was added dropwise thereto under ice cooling. After the addition, the temperature of the reaction solution was elevated to room temperature, and 3.4 g of 1-(4-nitrophenyl)ethyl bromide synthesized in the above-mentioned section (1) was added thereto, followed by stirring at room temperature for 20 hours in an atmosphere which was shielded from light. The resulting reaction mixture was poured into 1N hydrochloric acid slowly, and the solution was then extracted twice with 50 ml of ether. Extracts were joined together, washed with water and then dried over anhydrous sodium sulfate, and the solvent was distilled off under reduced pressure. The solution was then evaporated to dryness, thereby obtaining 3.9 g of dimethyl 1-(4-nitrophenyl)ethylmalonate in an oily state.

Analytical results of the obtained malonic derivative

NMR (CDCl$_3$) δ ppm: 1.38 (m, 3 H), 3.53 (s, 3 H), 3.81 (s, 3 H), 3.63–3.76 (m, 2 H), 7.43 (d, 2 H), 8.21 (d, 2 H).

(3) Preparation of methyl 3-(4-nitrophenyl)butyrate 3.45 g of lithium chloride and 0.7 g of water were added to 20 ml of a dimethyl sulfoxide solution containing 3.0 g of dimethyl 1-(4-nitrophenyl)ethylmalonate obtained in the above-mentioned section (2), and the solution was then heated at 170° C. for 1 hour under a nitrogen atmosphere. After standing for cooling, the reaction solution was poured into 100 ml of water, and extraction was then carried out twice with 50 ml of ether. The resulting organic layers were separated and joined together Then, the resulting solution was washed with water, and then dried over anhydrous sodium sulfate, and the solvent was distilled off. The resulting residue was purified through a silica gel column chromatograph (n-hexane/chloroform=1/5 to 1/100 in volume ratio), thereby obtaining 1.5 g of methyl 3-(4-nitrophenyl)butyrate in an oily state.

Analytical results of the obtained ester derivative

NMR (CDCl$_3$) δ ppm: 1.35 (d, 3 H), 2.61 (d, 2 H), 3.06–3.56 (m, 1 H), 3.60 (s, 3 H), 7.33 (d, 2 H), 8.10 (d, 2 H).

(4) Preparation of N-(2-hydroxyethyl)-3-(4-nitrophenyl)butylamine

A mixture of 1.5 g of methyl 3-(4-nitrophenyl)butyrate obtained in the above-mentioned section (3) and 5 ml of ethanolamine was heated at 100° C. for 4 hours under a nitrogen atmosphere The reaction mixture was poured into 50 ml of water, and potassium carbonate was added to the resulting aqueous solution until saturation was attained The solution was then extracted with 30 ml of chloroform twice. Chloroform layers were joined together and then dried over anhydrous sodium sulfate, and the solvent was distilled off under reduced pressure. The residue was added stepwise to 10 ml of a tetrahydrofuran solution containing 0.63 g of sodium borohydride under ice cooling, and 10 ml of a tetrahydrofuran solution containing 1 g of acetic acid was further added stepwise thereto over about 40 minutes. Next, the reaction solution was stirred for 1 hour while heated at 40° C., and its temperature was further elevated, followed by heating under reflux for 1 hour. Afterward, the reaction solution was ice-cooled, and 0.3 g of water was added stepwise thereto over about 10 minutes. Moreover, 10 ml of water and 1.5 g of 4N hydrochloric acid were added to the solution, and tetrahydrofuran was distilled off under reduced pressure A dilute sodium hydroxide solution was added to the resulting aqueous solution so as to make it alkaline, and this solution was then extracted with 20 ml of chloroform. The chloroform extract was washed with water, and then concentrated. The resulting residue was then recrystallized from toluene to obtain 0.9 g of crystalline N-(2-hydroxyethyl)-3-(4-nitrophenyl)butylamine.

(5) Preparation of 1,3-dimethyl-6-[2-(N-[2hydroxyethyl]-3-(4-nitrophenyl)butylamino)ethylamino]-2,4(1H,3H)-pyrimidinedione.fumarate (Compound 12)

0.9 g of 1,3-dimethyl-6-(2-methanesulfonyloxyethylamino)-2,4(1H,3H)-pyrimidinedione (Compound a) obtained in the section (1) of Example 11 and 0.67 g of potassium carbonate were suspended in 15 ml of acetonitrile, and the suspension was then heated under reflux for 4 hours under a nitrogen atmosphere. After standing for cooling, insolubles were removed from the solution by filtration. The filtrate was then concentrated, and 0.8 g of N-(2-hydroxyethyl)-3-(4-nitrophenyl)butylamine obtained in the above-mentioned section (4), 1.6 ml of dimethylformamide and 0.03 g of p-toluenesulfonic acid.monohydrate were added to the resulting residue, followed by stirring at 80° C. for 2 hours. After standing for cooling, the reaction solution was dissolved in 50 ml of chloroform, and the chloroform solution was then washed with an aqueous sodium carbonate solution and then water. Afterward, the solvent was distilled off under reduced pressure. The resulting residue was purified through a silica gel column chromatograph (chloroform/methanol=100/1 to 20/1 in volume ratio), thereby obtaining 1.2 g of 1,3-dimethyl-6-[2-(N-[2-hydroxyethyl]-3-(4-nitrophenyl)butylamino)ethylamino]-2,4(1H,3H)-pyrimidinedione in a light yellow oily state.

Analytical results of the obtained pyrimidinedione derivative

NMR (CDCl$_3$) δ ppm: 1.27 (d, 3 H), 1.84 (m, 2 H), 2.27–3.2 (m, 10 H), 3.27 (s, 3 H), 3.39 (s, 3 H), 3.62 (m, 2 H), 4.74 (s, 1 H), 5.97 (s, 1 H), 7.34 (d, 2 H), 8.16 (d, 2 H).

Furthermore, 1.15 g of this pyrimidinedione derivative was treated with a fumaric acid/methanol solution in an ordinary manner to prepare 0.9 g of crystals of 1,3-dimethyl-6-[2-(N-[2-hydroxyethyl]-3-(4-nitrophenyl)butylamino)ethylamino]-2,4(1H,3H)-pyrimidinedione.fumarate (Compound 12).

Analytical results of the obtained Compound 12

Melting point: 112° to 115° C.

Values of elemental analysis (as $C_{20}H_{29}N_5O_5 \cdot C_4O_4H_4 \cdot \frac{1}{2}H_2O$) Calcd. (%): C. 52.94; H 6.29;N 12.86; Found (%): C. 52.86; H 5.84;N 12.89.

EXAMPLE 13

Production of tablets containing, as an effective ingredient, 1,3-dimethyl-6-(4-[2-hydroxy-4-phenylbutyl)-piperazin-1-yl)-2,4(1H,3H)-pyrimidinedione.hydrochlordide (compound 1) which can be obtained by the procedure of Example 1:

With 20 g of corn starch were sufficiently mixed 1 g of the above pyrimidinedione derivative.hydrochloride (Compound 1) and 123 g of lactose, and the mixture was further mixed with a solution prepared by dissolving 5 g of hydroxypropyl cellulose in 100 ml of water, to form grains, followed by drying the grains at 50° C. for 4 hours. Afterward, 1 g of magnesium stearate was added to the dried grains, and they were mixed sufficiently. The mixture was then formed into tablets by the use of a tableting machine, the weight of each tablet being 150 mg.

EXAMPLE 14

Preparation of capsules containing, as an effective component, 1,3-dimethyl-6-[4-(1-ethoxycarbonyl-2-phenylethyl)piperazin-1-yl]-2,4(1H,3H)-pyrimidinedione.hydrochloride (Compound 6) which can be obtained by the procedure of Example 6:

With 25 g of corn starch were sufficiently mixed 5 g of the above pyrimidinedione derivative.hydrochloride (Compound 6) and 120 g of lactose, and hard capsules were filled with the resultant mixture by the use of a capsule filling machine to obtain capsules, the content of the mixture in each capsule being 150 mg.

EXAMPLE 15

Preparation of an injection containing, as an effective component, 1,3-dimethyl-6-[4-(1-ethoxycarbonyl- 2-phenylethyl)piperazin-1-yl]-2,4(1H,3H)-pyrimidinedione.hydrochloride (Compound 6) which can be obtained by the procedure of Example 6:

In a suitable amount of distilled water for injection were dissolved 20 mg of the above pyrimidinedione derivative.hydrochloride (Compound 6) and 0.85 g of sodium chloride, and the total volume of the liquid was then regulated to be 100 ml, thereby preparing an injection.

Pharmacological Test

Influence on myocardial action potential duration time ($APD_{75}$):

To a hybrid adult dog, 30 mg/kg of pentobarbital was administered through a vein, and after being anesthetized, the heart was removed. Afterward, the right ventricular free wall of the heart was cut and taken out in a Tyrode solution.

The taken right ventricular free wall was fixed in an incubator at 37° C., and a nutritional solution (20 ml of the Tyrode solution) was refluxed.

In this isolated condition, myocardial action potential duration times ($APD_{75}$) were measured before and after the administration of the respective compounds prepared in the above examples in Table 1 and d-sotalol as a control medicine, and $APD_{75}(\%)$ was calculated from the measured results in accordance with the formula:

$$APD_{75}(\%) = (B-A)/A \times 100$$

A: $APD_{75}$ before administration
B: $APD_{75}$ after administration

Here, $APD_{75}$ was measured as follows: A field stimulation of 1 Hz was given to the right ventricular free wall, and any variation of an action potential was depicted on an oscilloscope via a glass microelectrode (10 to 20 MΩ) thrust into a Purkinje fiber of the free wall and via an amplifier. Afterward, a waveform on the oscilloscope was analyzed by the use of a computer, and the time of from a point of the action potential generation to a point of 75% repolarization was measured. This measured time was regarded as the myocardial action potential duration time ($APD_{75}$).

Each of the compounds shown in Table 1 was separately added to the refluxing nutritional solution (20 ml), and after 20 minutes' incubation, $APD_{75}$ after the administration was calculated from the variation of the myocardial action potential duration time.

Incidentally, this test was carried out in accordance with a Sato et al's method [H. Sato, K. Hashimoto, Arzneimeittel Forschung, 34 (1), 3a, 376-380 (1984)].

The obtained results are set forth in Table 1.

TABLE 1

| | (results of pharmacological test) | | | |
|---|---|---|---|---|
| Compound No. | $APD_{75}$ (%) Dose (μg/ml) | | | |
| | 0.3 | 1.0 | 3.0 | 10.0 |
| 1 | — | 3 | 6 | 15 |
| 4 | — | 6 | 9 | 12 |
| 8 | — | — | 9 | 15 |
| 10 | — | — | 15 | 17 |
| d-sotalol | 0 | 3 | 7.4 | 15.8 |

What is claimed is:

1. A pyrimidinedione derivative represented by the formula:

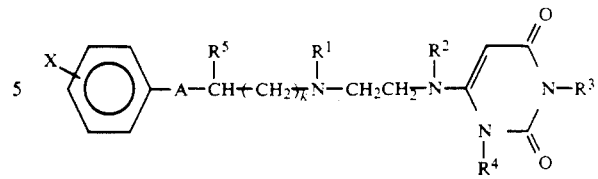

wherein
A is —$(CH_2)_n$—,

or —O—$(CH_2)_m$—;
each of $R^1$ and $R^2$ is independently a hydrogen atom or a lower alkyl group which may be substituted by a hydroxyl group, or $R^1$ and $R^2$ may be so lined with each other as to make an ethylene chain and thus form a six membered 1,4-diazine ring structure;
each of $R^3$ and $R^4$ is independently a hydrogen atom or a lower alkyl group;
$R^5$ is a halogen atom, a hydroxyl group, a lower alkoxycarbonyl group or a lower alkyl group which may be substituted by a hydroxyl group, or when $R^1$ is not linked to $R^2$, $R^5$ may be so linked with $R^1$ as to make an ethylene chain and thus form a piperidine structure;
X is a hydrogen atom, a halogen atom or a nitro group;
N is 0, 1, 2 and 3 provided that when $R^5$ is a hydroxyl group, n≠0;
m is 0, 1, 2 or 3; and
k is 0, 1, 2 or 3, provided that when $R^5$ is hydroxyl A is not —O—$(CH_2)_m$—.

2. A pharmaceutically acceptable acid addition salt of said pyrimidinedione derivative described in claim 1.

3. An antiarrythmic agent containing, as an effective component, one or more compounds selected from the group consisting of the pyrimidinedione derivatives described in claim 1 and the pharmaceutically acceptable acid addition salts described in claim 2.

4. A method of treating cardiac arrhythmias comprising administering to a person in need of same an effective amount of the compound of claim 1 or the acid addition salt of claim 2.

* * * * *